United States Patent [19]

Tanaka et al.

[11] 4,014,941
[45] Mar. 29, 1977

[54] METHOD OF PRODUCING α,β-UNSATURATED ETHER

[75] Inventors: Kazuaki Tanaka; Yasuto Ishida; Kimiyoshi Yanagi, all of Yokkaichi; Noriaki Kassai, Kameyama; Toshiyuki Tanaka, Yokkaichi, all of Japan

[73] Assignee: Kyowa Yuka Co., Ltd., Japan

[22] Filed: Feb. 28, 1974

[21] Appl. No.: 446,764

Related U.S. Application Data

[63] Continuation of Ser. No. 203,897, Dec. 1, 1971, abandoned.

[30] Foreign Application Priority Data

Dec. 11, 1970 Japan .................... 45-109337

[52] U.S. Cl. ................................ 260/614 R
[51] Int. Cl.² ............................... C07C 41/00
[58] Field of Search ........................... 260/614

[56] References Cited

UNITED STATES PATENTS

| | | | |
|---|---|---|---|
| 2,290,211 | 7/1942 | Schaad | 252/437 |
| 2,470,190 | 5/1949 | Schmerling | 252/437 |
| 3,285,967 | 11/1966 | Schaeffer | 260/614 R |

FOREIGN PATENTS OR APPLICATIONS

| | | | |
|---|---|---|---|
| 1,253,965 | 1/1961 | France | 260/614 R |
| 41-5376 | 3/1966 | Japan | 260/614 R |

*Primary Examiner*—Howard T. Mars
*Attorney, Agent, or Firm*—Craig & Antonelli

[57] ABSTRACT

A method of producing α,β-ethylenically unsaturated ethers, which comprises decomposing an acetal having at least one hydrogen atom bonded to a carbon atom contiguous to the carbon atom of the group

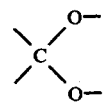

in its molecule in the presence of a calcium phosphate catalyst to produce a reaction product containing the corresponding α,β-ethylenically unsaturated ether.

13 Claims, No Drawings

METHOD OF PRODUCING α,β-UNSATURATED ETHER

This is a continuation of application Ser. No. 203,897 filed Dec. 1, 1971 and now abandoned.

This invention relates to a method of producing α,β-ethylenically unsaturated ethers. More particularly, this invention relates to a method of producing α,β-ethylenically unsaturated ethers by subjecting acetals to a catalytic decomposition reaction using a solid catalyst of calcium phosphate.

Heretofore several methods have been proposed for producing α,β-unsaturated ethers. For example, such known methods include those based on the high pressure reaction of acetylene with alcohol or the catalytic reaction of ethylene with alcohol using palladium. However, these methods have disadvantages such as the high cost of acetylene in the former method and the low yield and the considerable formation of by-products in the latter method. Therefore, these two methods are not considered economically advantageous.

Besides these methods, there is another method of producing α,β-unsaturated ethers based on catalytic or thermal decomposition of acetals easily synthesized from aldehydes and alcohols in liquid or gaseous phase. Since various aldehydes including acetaldehyde are now obtained at industrially low costs, this method is of high value from the industrial point of view. The catalysts used for producing an α,β-unsaturated ether by decomposing an acetal in gaseous phase are described in Japanese Patent Publication No. 5376/66 and U.S. Pat. No. 3,285,967. In both cases, in order to increase the selectivity to the desired product, i.e. the α,β-unsaturated ether, by suppressing the side reactions, it is necessary to control the conversion of the acetal below 80 % by maintaining the reaction temperature at about 250° C. If the reaction temperature is elevated to about 300° C. in order to get a higher conversion, side reactions take plce with considerable formation of by-products. Moreover, the presence of the by-products results in such an industrial disadvantage that the process for separating pure α,β-unsaturated ether, the desired product, from the reaction product becomes complicated. If no side reactions occur, it is industrially very advantageous because the reaction product comprises only α,β-unsaturated ether, alcohol and a trace of unreacted acetal. Consequently, the process for separating pure α,β-unsaturated ether from this reaction product becomes simple.

The present inventors have conducted extensive experiments and studied to develop a catalyst that brings about a high yield of α,β-unsaturated ethers and besides, no side reactions in decomposing acetal. As the results, the inventors have found that calcium phosphate either alone or supported on a solid carrier provides an excellent catalyst that results in almost no side reactions when the catalytic decomposition of the acetal is carried out at a temperature as high as 280° C. Moreover, in the operation using an industrially advantageous fixed-bed reactor, the catalyst shows an extended catalyzing activity which is an essential condition. Specifically, the catalytic life is on the order of 2,000 hours or more. The life of other catalysts is not comparable with this value.

The acetal used as a starting material or reactant in the method of the present invention must be one that has at least one hydrogen atom bonded to one of the carbon atoms directly adjacent to the carbon atom of the group

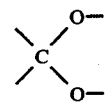

in its molecule.

More specifically, the starting acetal used in the present invention is one having the formula:

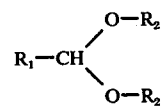

wherein $R_1$ is an alkyl group having 1 to 3 carbon atoms and $R_2$ is an alkyl group having 1 to 4 carbon atoms.

This acetal is derived from aldehydes containing from 2 to 8 carbon atoms and preferably from those containing 2 to 4 carbon atoms e.g. an alkanol such as acetaldehyde, propionaldehyde, isobutylaldehyde, butylaldehyde, and the like and one of the saturated or unsaturated fatty alcohols containing from 1 to 6 carbon atoms and preferably containing 1 to 4 carbon atoms e.g. an alkanol such as methanol, ethanol, isobutanol, an alkanol such as allyl alcohol and the like. Thus, it will be appreciated that the alkoxy groups formed in the acetal by the alcohols are acyclic radicals which may be straight or branched chain groups.

As examples of particularly effective acetals, there are given dimethyl-, diethyl-, dipropyl-, diisobutyl- and diallyl-acetal derived from acetaldehyde. It will be understood that the acetals employed may contain from 4 to 25 carbon atoms.

The ethers i.e. the objective products of the present method are those that have an unsaturated double bond at the α,β-position corresponding to the employed acetals above-mentioned. Exemplary of these ethers are methyl vinyl ether, ethyl vinyl ether, propyl vinyl ether, isobutyl vinyl ether, allyl vinyl ether, ethyl propenyl ether and the like. Other ether products include amyl vinyl ether, amyl propenyl ether, methyl 1-butenyl ether, ethyl-1-hexenyl ether and the like.

The α,β-unsaturated ethers, the products of this invention, provide useful materials for producing synthetic resins, bonding agents, etc. as a result of homo- or co-polymerization. Further, the ether is useful as an internal plasticizer of a synthetic rubber, a polymer of vinyl chloride, etc., or as an intermediate in the synthesis of organic compounds.

As heretofore described, the catalyst used in the method of the present invention is a calcium phosphate either alone or supported on a carrier. The "calcium phosphate" means anhydrous or hydrated forms of calcium dihydrogenphosphate $Ca(H_2PO_4)_2$, calcium monohydrogenphosphate $CaHPO_4$, calcium phosphate $Ca_3(PO_4)_2$, meta-calcium phosphate $Ca(PO_3)_2$, pyro-calcium phosphate $CaP_2O_7$ or calcined products thereof.

As for the carrier support, materials used as carriers in usual catalytic reactions may be employed. However, those which do not cause side reactions such as decomposition and dehydration of the α,β-unsaturated ether product and alcohols, are most desirable. For example, alumina, asbestos, pumice, unglazed ceramics are suitable carriers for the calcium phosphate catalyst.

The size of the catalyst particles is properly decided depending upon the type of the operation. However, there is no strict requirement. When, for example, a catalyst having 2 to 100 mesh size is employed in a fixed-bed reactor, a satisfactory result is obtained. Any reaction temperatures above the boiling point of the acetal used as the starting material and below the degradation temperature of the ether product may be employed. A temperature ranging from 200° to 350° C. is most suitable. A continuous operation may be possible by supplying the raw starting material, i.e. the acetal, successively into the reaction zone kept at a fixed temperature. In such a case, it is preferable to preheat the acetal before supplying it into the reaction zone.

The reactor may be either a fixed-bed type or a fluid-bed type, but the fixed-bed type which is easy to operate may be often the most satisfactory. The reaction pipes can be positioned either vertically or horizontally.

As to the reaction pressure, operation under an atmospheric pressure provides satisfactory results. The reaction may be, however, carried out under a reduced or an increased pressure according to particular circumstances, e.g. from 0.1 to 50 atm. for the vapor phase reaction.

Furthermore, it is possible to supply the starting material, i.e. the acetal into the reaction zone accompanied with a diluting agent which is an inert substance that is gaseous at the reaction temperature. Such gases as nitrogen, helium, argon, and the like or organic substances such as diethyl ether, dibutyl ether, and the like have been found suitable for this purpose.

The amount of acetal charged to the reactor can be varied depending upon the size of the reaction pipes and the amount is usually in the range of 0.001 – 1 mol. per hour per one gram of the catalyst. Most preferably the acetal is used in an amount within the range of from 0.01 to 0.1 mol. per hour per gram catalyst.

The reaction product produced by the catalytic decomposition of the acetal is condensed by cooling and then the condensate is subjected to a fractional distillation whereby the objective product, i.e. the $\alpha,\beta$-ethylenically unsaturated ether is easily recovered.

The invention will be understood in greater detail by reference to the following examples which are intended to be merely illustrative and not limitative thereof.

EXAMPLE 1

Powdered anhydrous calcium phosphate $Ca_3(PO_4)_2$ was shaped by pressing and then pulverized into 8 – 10 mesh granules. The resulting granules were calcined at 500° C. for two hours in a nitrogen atmosphere. 10 g (20 cc) of the catalyst was charged in the reaction pipe which was 25 mm. in inner diameter and 400 mm. in length. While the catalyst layer being kept at 280° C. in an electric furnace, acetaldehyde diisobutyl acetal in gaseous phase was passed through the catalyst bed at a rate of 35 g per hour (0.20 mol. per hour) and the catalytic reaction was continued for 4 hours. The reaction product coming out from the reactor was condensed by cooling and 139.9 g of a liquid product was obtained. The product was subjected to a fractional distillation to give 79.1 g of isobutyl vinyl ether, 58.6 g of isobutanol and 2.2 g of unreacted diisobutyl acetal. The conversion of the acetal was found as 98.4 % and the selectivity to the vinyl ether as 100 %.

EXAMPLES 2–4

Catalysts of different calcium phosphates were prepared in the same manner as in Example 1, and the same reactions as in Example 1 were carried out using the same reactor. The reaction conditions were also the same as in Example 1, except that the temperature of each reaction was 240° C. The results are given in the following table:

| Example No. | Catalyst | Conversion of Acetal(%) | Selctivity to Vinyl ether(%) |
|---|---|---|---|
| 2 | Calcium dihydrogen-phosphate $Ca(H_2PO_4)_2$ | 91.5 | 98.4 |
| 3 | Calcium monohydrogenphosphate $CaHPO_4$ | 90.6 | 99.9 |
| 4 | Calcium phosphate $Ca_3(PO_4)_2$ | 91.8 | 100.0 |

The catalysts noted were all prepared from anhydrous materials, but even in additional experiments where the catalysts were prepared from hydrates and were used in the same procedure the results of the reactions were the same as above.

EXAMPLE 5

In this example, a catalyst obtained by adding an aqueous solution containing 3 g of calcium phosphate $Ca_3(PO_4)_2$ to 10 g of cotton-like asbestos of a carrier, followed by drying to make the calcium phosphate $Ca_3(PO_4)_2$ supported on the carrier and by calcining the resulting composite in a nitrogen atmosphere at 300° C. for 2 hours, was employed. As a result of carrying out the same reaction under the same conditions as in Example 1, the conversion of the acetal, i.e. acetaldehyde diisobutyl acetal was 95.4 % and the selectivity to isobutyl vinyl ether was 97.8 %.

EXAMPLE 6

A catalytic reaction was carried out using the catalyst prepared in the same manner as in Example 1 and acetaldehyde diethyl acetal as a raw material under the same conditions as in Example 1. The conversion of diethyl acetal of 98.1 % and the selectivity to ethyl vinyl ether of 96.5 % were obtained.

EXAMPLE 7

A reaction was carried out using as a raw material propionaldehyde diethyl acetal synthesized with propionaldehyde and ethanol by a conventional method. The employed catalyst was calcium phosphate $Ca_3(PO_4)_2$ prepared in the same manner as in Example 1. The reaction conditions were the same as in Example 1 except that the reaction temperature was 260° C. and the rate of supplying the raw material was 26 g per hour. 207 g of the reaction product obtained by carrying out the reaction for 8 hours was subjected to a fractional distillation to give 123.6 g of ethyl propenyl ether, 77.0 g of ethanol and 6.0 g of unreacted acetal. The conversion of the acetal was 92.3 % and the selectivity to ethyl propenyl ether was 98.8 %.

EXAMPLE 8

In this example, a reaction was carried out at 220° C. using the catalyst, calcium phosphate $Ca_3(PO_4)_2$ prepared in the same manner as in Example 1 and the reaction was continued for 2,000 hours without any changes of the catalytic activity and the catalytic selectivity. The reaction conditions were the same as in Example 1 except the reaction temperature, and acetaldehyde diisobutyl acetal was used as a raw material. The results are as follows.

| Reaction time | Conversion of acetal (%) | Selectivity to vinyl ether (%) |
|---|---|---|
| 100 | 80.3 | 99.2 |
| 500 | 81.1 | 99.2 |
| 1,000 | 79.9 | 99.1 |
| 2,000 | 79.7 | 99.4 |

EXAMPLE 9

A reaction was carried out using n-butylaldehyde di-n-butyl acetal as the raw material. The employed catalyst was anhydrous calcium phosphate $Ca_3(PO_4)_2$ not calcined. The reactor and the reaction conditions were the same as in Example 1 except that the reaction temperature was 300° C. As a result, n-butenyl n-butyl ether ($CH_3CH_2CH=CHOC_4H_9$) was obtained as a main product. The conversion of the acetal was found as 97.9% and the selectivity to the vinyl ether as 90.4%.

EXAMPLE 10

A reaction was carried out in the same manner as in Example 1 except that the employed catalyst was charged in the reaction pipe without being calcined and the reaction temperature was 270° C. The conversion of the acetal was found as 93.0% and the selectivity to the vinyl ether as 99.1%.

EXAMPLE 11

Anhydrous calcium phosphate $Ca_3(PO_4)_2$ and graphite (100:5) were well mixed. The mixture was shaped by pressing into 5mm × 5mm size pellets. 90 g of the pellets was charged in the quartz reaction pipe which was 30 mm in inner diameter and 1,000 mm in length. While the catalyst layer being kept at 250° C., acetaldehyde diisobutyl acetal was passed through the catalyst bed at a rate of 136 g per hour (0.78 mol. per hour). The conversion of the acetal was found as 94.0% and the selectivity to the vinyl ether as 99.5%.

What is claimed is:
1. A method for producing an $\alpha,\beta$-ethylenically unsaturated ether comprising decomposing an acetal having the formula:

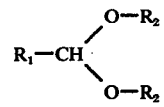

wherein $R_1$ is an alkyl group having 1 to 3 carbon atoms and $R_2$ is an alkyl group having 1 to 4 carbon atoms, at a temperature from 200° to 350° C. in the presence of a catalyst selected from hydrous or anhydrous $Ca_3(PO_4)_2$, $Ca(H_2PO_4)_2$ and $CaHPO_4$ or calcined products thereof either alone or supported on a carrier selected from alumina, asbestos, pumice and unglazed ceramics to produce a reaction product comprising the corresponding $\alpha,\beta$-ethylenically unsaturated ether, 0.001 to 1 mol of said acetal being contacted with each gram of catalyst per hour, said catalyst having a size of 2 to 100 mesh.

2. The method of claim 1, wherein the $\alpha,\beta$-ethylenically unsaturated ether is recovered from the reaction product by fractional distillation.

3. The method of claim 1, wherein the acetal is decomposed at a pressure ranging from 0.1 to 50 atm.

4. The method of claim 3, wherein the acetal is decomposed at atmospheric pressure.

5. The method of claim 1, wherein said carrier is cotton-like asbestos.

6. The method of claim 1, wherein said carrier is pumice.

7. The method of claim 1, wherein said carrier is unglazed ceramics.

8. The method of claim 1, wherein 0.01 to 0.1 mol of said acetal is contacted with each gram of catalyst per hour.

9. The method of claim 8, wherein said carrier is cotton-like asbestos.

10. The method of claim 8, wherein said carrier is pumice.

11. The method of claim 8, wherein said carrier is unglazed ceramics.

12. The method of claim 8, wherein the acetal is decomposed at a pressure ranging from 0.1 to 50 atm.

13. The method of claim 12, wherein the acetal is decomposed at atmospheric pressure.

* * * * *